(12) United States Patent
Burmer et al.

(10) Patent No.: US 6,183,995 B1
(45) Date of Patent: Feb. 6, 2001

(54) METHODS OF MEASURING GENE EXPRESSION USING WAX-EMBEDDED TISSUE SPECIMENS

(75) Inventors: Glenna C. Burmer, Seattle; Amanda A. Ford, Carnation; Joseph P. Brown, Seattle, all of WA (US)

(73) Assignee: LifeSpan BioSciences, Inc., Seattle, WA (US)

(*) Notice: Under 35 U.S.C. 154(b), the term of this patent shall be extended for 0 days.

(21) Appl. No.: 08/925,818

(22) Filed: Sep. 5, 1997

(51) Int. Cl.[7] .............. C12P 19/34; C12Q 1/68; G01N 33/567; C07H 21/04
(52) U.S. Cl. ............ 435/91.1; 435/91.2; 435/91.5; 435/91.51; 435/6; 436/94; 436/503; 536/23.1; 536/24.2; 536/24.3; 536/24.33; 536/25.32
(58) Field of Search ................... 435/91.1, 91.2, 435/91.5, 91.51, 6; 436/503, 94, 503.94; 536/23.1, 24.2, 24.3, 24.33, 25.32; 935/77, 78, 86, 87; 422/68.1

(56) References Cited

U.S. PATENT DOCUMENTS 5,690,894 * 11/1997 Pinkel et al. .............. 422/68.1
5,759,822 * 6/1998 Chenchick et al. ......... 435/91.2
5,871,697 * 2/1999 Rothberg et al. .......... 422/68.1

OTHER PUBLICATIONS

Jiang, Y.H., et al., Nucleic Acids Research, vol. 23, "A rapid RT–PCR method for detection of intact RNA in formalin–fixed paraffin–embedded tissues", pp. 3071–3072, 1995.*
Nuovo, G. J., PCR Methods and Applications, vol. 4, "In situ PCR: Protocols and Applications", pp. S151–S167, 1995.*
Spellman, J. E., et al., Surgical Oncology, vol. 5, "Cytokine production by human soft tissue sarcomas: implications for tumor suppression with the tumour bed", pp. 237–244, 1996.*
Cardillo, M.R. et al., *J. Exp. Clin. Cancer Res.* 16, 1:49 (1997).
Dakhama, Azzeddine et al., *The Journal of Histochemistry and Cytochemistry* 44:1205 (1966).
Edelstein, Robert A. et al., *Urology* 45:597 (1995).
Finke, J. et al., *BioTechniques* 14:448 (1993).
Foss, Robert D., *Diagnostic Molecular Pathology* 3(3) :148 (1994).
Hodges, Elizabeth et al., *Leukemia Research* 19:183 (1995).
Houze, Thomas A. et al., *BioTechniques* 21:1074 (1996).
Houze, Thomas A. et al., *Tumor Biol* 18:53 (1997).
Mee, A.P., et al., *Journal of Molecular Endocrinology* 16:183 (1996).
Mies, Carolyn, *The Journal of Histochemistry and Cytochemistry* 42:811 (1994).
Peters, Jochen et al., *American Journal of Pathology* 150:469 (1997).
del Prozo, Victoria et al., *Toxicology* 118:61 (1997).
Smith, Malcolm et al., *Diagn Mol Pathol.* 6:34 (1997).
Stanta, Giorgio et al., *BioTechniques* 11:304 (1991).
Szakacs, Juliana G. et al., *Annals of Clinical and Laboratory Science* 24:324 (1994).
Tyrrell, Lynda et al., *The American Journal of Dermatopathology* 17 (5) :476 (1995).
Weizsäcker, F. v. et al., *Biochemical and Biophysical Research Communications* 174:176 (1991).

* cited by examiner

Primary Examiner—Ponnathapu Achutamurthy
Assistant Examiner—William W. Moore
(74) Attorney, Agent, or Firm—Townsend and Townsend and Crew LLP

(57) ABSTRACT

This invention provides methods for the isolation of complete representation of cellular messenger ribonucleic acid from wax-embedded tissue samples. Expression of genes of interest can thus be fortuitously determined and cDNA probes can be readily developed.

16 Claims, 2 Drawing Sheets

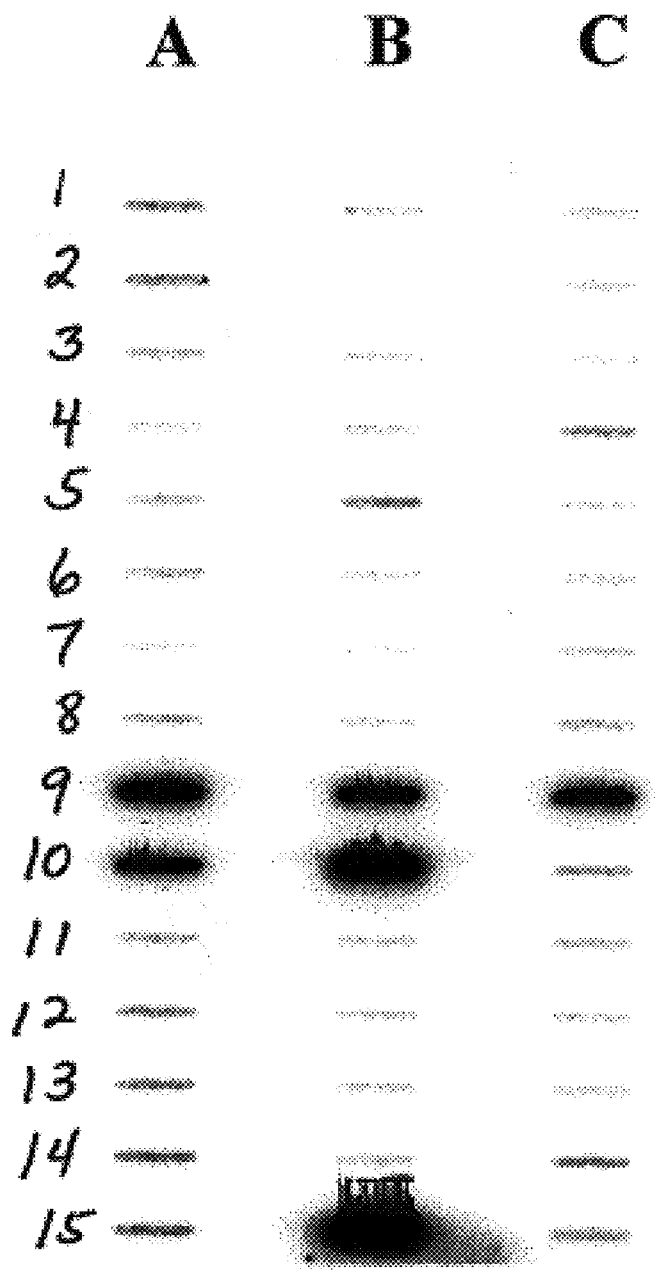
Figure 2. Slot Blot Hybridized With GTPase, KIAA, ORP

METHODS OF MEASURING GENE EXPRESSION USING WAX-EMBEDDED TISSUE SPECIMENS

BACKGROUND OF THE INVENTION

Wax-embedded tissue samples are convenient reservoirs of nucleic acid information. The presence of mRNA in such samples can provide extremely useful information about the expression of genes in certain cell types that have been preserved in this manner. However, when efforts have been made to obtain information about the mRNA in such samples, it is clear that extensive degradation of the cellular RNA exists.

Some researchers have reported detection of mRNA in such preserved tissues by in situ hybridization. Efforts have been made to extract mRNA from such samples and individual species of certain mRNA have been detected by PCR, however, these efforts are generally limited because the mRNA is degraded to small fragments usually less than 200 or 250 nucleotides in length. Because of the extent of degradation of the mRNA, efforts to attempt to obtain a representation of all species of mRNA from such samples have been deemed to be futile.

Further, about 95% of cellular RNA is ribosomal RNA (rRNA). Separation of the mRNA from the rRNA is difficult in samples such as these. The rRNA needs to be eliminated in gene expression studies because it does not reflect expression of the cellular genes. Common methods for separating mRNA from rRNA, such as the oligo (dT) method, operate by selecting for polyadenylated RNA. These methods are not very effective in these types of preserved cell samples. They automatically exclude much of the mRNA because the degradation which has occurred in the sample results in a high percentage of mRNA that does not have a polyA tail.

Also, when RNA is being studied, DNA must be removed to prevent background problems that result from its presence. Though RNA is typically separated from DNA by precipitating it away from the DNA, this method has the disadvantage that the RNA fragments which are obtained are of the same or similar size thus, limiting the representation of the total RNA population. Since paraffin-embedded tissues are a relatively convenient source of a variety of tissue types, it would be highly desirable to develop a method of obtaining a complete representation of the cellular mRNA from paraffin-embedded tissue samples for genomic analysis.

SUMMARY OF THE INVENTION

Our methods for extraction of mRNA from wax-embedded tissues and methods for production of resultant cDNA probes from such mRNA overcome the problems in the prior art, in part, by taking advantage of the fragmentation and degradation of the resident mRNA. The present degraded fragments of mRNA are readily copied and amplified without bias or omission. The methods described here can provide a complete representational library of cellular mRNA which can be copied to cDNA for multiple uses such as probes. The cDNA represents a reflection of the genes which are expressed in the source material and enables the genomic analysis of such material. Further, it was surprising that our methods did not result in much contamination from rRNA since none of the steps in the method are specifically directed to its removal, or at least not in the traditional way through the selection of polyadenylated RNA. Our methods also demonstrate that DNase may effectively be used in combination with our extraction method to reduce the background noise caused by DNA.

Specifically, the invention relates to a method for the production of cDNA representative of complete representational cellular mRNA from a wax-embedded biological sample wherein the RNA is extracted from the wax-embedded sample by removing the DNA in the biological sample with a DNAse and without a step to selectively eliminate rRNA by selection for polyadenylated RNA to produce sample cellular RNA. A strand of cDNA complementary to the sample cellular RNA is synthesized by contacting the sample RNA to one or more oligonucleotides and a reverse transcriptase to create single strand cDNA copies of the cellular RNA. The cDNA may then optionally be isolated by selectively separating the cellular RNA from the cDNA copies. The cDNA may be directly useful as probes, particularly if it is synthesized using labeled oligonucleotides or dNTPs. Complementary strands of the cDNA copies may be synthesized to create double-stranded cDNA. The double-stranded cDNA is preferably amplified by ligating a pair of complementary oligonucleotide adaptors to the double-stranded cDNA. The adaptors will be such that they are of different lengths. The cDNA copies may be amplified with a primer complementary to one of the adaptors.

The objectives of the methods of this invention are accomplished best when the adaptors used are blunt on one end and staggered on the other. The use of such adaptors results in an unbiased amplification of the cDNA and provides a more accurate picture of the total resident cellular mRNA. Each resident cDNA fragment is equally likely to have the blunt adaptors ligated to it and thus, to be amplified. The use of adaptors that are sticky on both ends may be useful in some cases, for example where the source mRNA was not very degraded, but is less preferred where total cellular mRNA is truly desirable.

Thus, the methods herein will imply many uses for the resulting mRNA or cDNA. The mRNA from the wax-embedded samples can be employed in comparison assays with mRNA or cDNA from other wax-embedded samples or with mRNA, cDNA or DNA from other samples of known or unknown origin depending upon the information desired. Methods for determining the presence or absence of gene expression in a wax-embedded biological sample are described comprising screening cDNA probes derived from mRNA extracted from wax-embedded biological material against nucleic acid material containing a known gene of interest. The cDNA may also be screened against cDNA from other wax-embedded samples or other nucleic acid source to determine if the same nucleic acid is expressed in both samples. All of such screening can be advantageously conducted in a high density array arrangement and may be conducted against nucleic acid representative of different tissue types.

DESCRIPTION OF THE FIGURES

FIG. 2 represents an image demonstrating gene expression in amplified cDNA from 44 different paraffin archival diseased tissues in accordance with the methods of this invention when probed with nick-translated, radiolabeled cDNA for three different genes.

DETAILED DESCRIPTION OF INVENTION

Introduction

Figure 1:
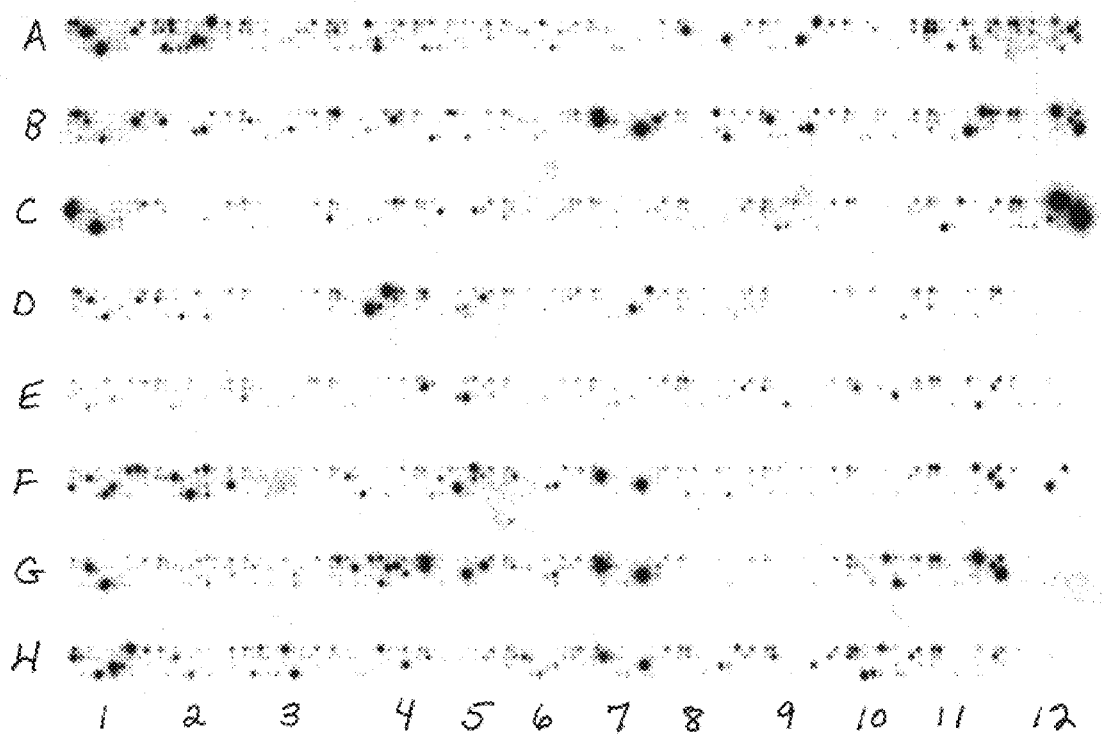
FIG. 1 represents an image of an array of 1000 different genes blotted onto a nylon membrane and probed with an amplified and nick-translated cDNA (radiolabeled) derived from a paraffin-embedded skin sample in accordance with the methods of the invention.

The invention describes a method of measuring the presence or absence and amount of gene expression using wax-embedded tissue specimens and a method of isolating a complete representation of cellular messenger ribonucleic acid (mRNA) from a biological sample. Using the methods described here, a complete representation of cellular mRNA can be isolated from a tissue sample. This embodiment differs from other methods of isolating cellular mRNA that typically separate mRNA from the ribosomal RNA (rRNA) by selecting for polyadenylated (Poly A) RNA. This selection method prevents the complete representation of the mRNA because mRNA is usually somewhat degraded in the tissue and mRNA without a Poly A tail is missed in the selection process. The present invention does not directly select out the mRNA, and so ends up with a complete representation of the cellular mRNA instead of only those portions that have retained the Poly A tail. By "complete representation of the cellular mRNA" it is meant that the cellular mRNA is nearly, if not completely, represented in the mRNA extracted and that no single cellular mRNA species is likely to be overlooked in the selection process.

In another embodiment, the present invention relies on the complete representation of cellular mRNA to compile a complete cDNA (copy deoxyribonucleic acid) probe library for gene expression in various diseases or tissue types of interest. For example, the methods of this invention permit analysis of a tissue bank of human tissue specimens representing multiple samples of all normal and disease tissue available. Drawing from these tissues, the invention provides a method of creating a library of cDNA probes for the diseases represented in the bank and a method of measuring the gene expression in the healthy and diseased tissues. Furthermore, due to the complete representation of cellular mRNA, the invention provides a complete cDNA library representing the gene expression in a particular tissue.

The importance of the instant invention is that no complete representations of cellular mRNA have been isolated before from wax samples. This isolation technique provides a complete representation of cellular mRNA and allows for the synthesis of a more complete cDNA library from such samples. In addition, the invention enables the use of actual human tissue samples as opposed to cell lines, yeast, invertebrate or animal models.

Another advantage of the present invention is its ability to identify gene expression in the healthy or diseased tissues at a level of one molecule of RNA per cell.

Definitions

"Biological sample" or "Biological Source" refers to any tissue or liquid sample from a source having nucleic acid.

As used herein, "cDNA" or "copy-DNA" or "complementary-DNA" refers to a DNA copy of an RNA, and is made from the RNA using reverse transcriptase. cDNA can be used as a probe to find an unknown gene in DNA.

The term "dNTPs" refers to a solution of deoxynucleotide triphosphates useful for nucleic acid synthesis. Typically it is recommended that the four nucleotides or their analogs be used at equivalent concentrations.

The term "gene" means the segment of DNA involved in producing a polypeptide chain; it includes regions preceding and following the coding region (leader and trailer) as well as intervening sequences (introns) between individual coding segments (exons).

The term "isolated", when applied to a nucleic acid or protein, denotes that the nucleic acid or protein is essentially free of other cellular components with which it is associated in the natural state. It is preferably in a homogeneous state although it can be in either a dry or aqueous solution. Purity and homogeneity are typically determined using analytical chemistry techniques such as polyacrylamide gel electrophoresis or high performance liquid chromatography.

A "label" as used herein is a moiety associated with a nucleic acid that allows detection of the nucleic acid by spectroscopic, photochemical, biochemical, immunochemical, or other chemical means. Useful nucleic acid labels can include enzymes (e.g., LacZ, CAT, horse radish peroxidase, alkaline phosphatase, and others, commonly used as detectable enzymes, either as marker gene products or in an ELISA), nucleic acid intercalators (e.g., ethidium bromide, psoralen), colorimetric labels such as colloidal gold or colored glass or plastic (e.g., polystyrene, polypropylene, latex, etc.,) beads, substrates, cofactors, inhibitors, or fluorescent moieties (e.g., fluorescein and its derivatives, rhodamine, danysl and the like), chemiluminescent moieties (e.g., luciferin and 2,3-dihydrophthalazinediones), radioactive labels, magnetic particles, and the like. Examples of direct ligand binding and detection include the use of biotin labeled nucleotides or the use of digoxigenin, including photobiotinylation. These molecules can be used as the ligand binding component. They can be readily captured by their anti-ligand, e.g. avidin or streptavidin in the case of biotin and an anti-digoxigenin antibody, bound on a suitable substrate. (These reagents are all readily available, see Clontech Laboratories, Inc., Palo Alto, Calif. for digoxigenin reagents, for example.) Molecules which do not bind the anti-ligand can be collected and captured, by for example passing them through a streptavidin column. A wide variety of labels suitable for labeling nucleic acids and conjugation techniques for labeling the nucleic acids are reported extensively in both the scientific and patent literature. The choice of label depends on the sensitivity required, ease of conjugation of the compound, stability requirements, available instrumentation and disposal provisions.

Methods for detecting labels are well known to those of skill in the art. For example, radioactive labels can be detected by scintillation counter or photographic film as in autoradiography. Fluorescent labels may be detected by exciting the fluorochrome with the appropriate wavelength of light and detecting the resulting fluorescence, e.g, by microscopy, visual inspection, photographic film, or electronic detectors.

"Nick translation" refers to the process whereby double-stranded nucleic acid can be labeled by replacing preexisting nucleotides in one strand with radioactive (or other labeled nucleotides) when one of the strands of a double-stranded nucleic acid is nicked. DNA polymerase I adds nucleotide residues to the 3'-hydroxyl terminus that is nicked. The enzyme also by virtue of its 5' to 3' exonucleolytic activity, can remove nucleotides from the 5' side of the nick. The simultaneous elimination of nucleotides from the 5' side and the addition of nucleotides to the 3' side results in movement of the nick (nick translation) along the nucleic acid. Protocols for nick translation are described, for example, in Sambrook et. al., *Molecular Cloning A Laboratory Manual* Second Edition (1989), Cold Spring Harbor Laboratory Press.

The term "nucleic acid" refers to deoxyribonucleotides or ribonucleotides and polymers thereof in either single- or double-stranded form. Unless specifically limited, the term encompasses nucleic acids containing known analogues of a natural nucleotide which have similar binding properties as the reference nucleic acid and are metabolized in a manner similar to naturally occurring nucleotide. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); and Cassol et al., 1992; Rossolini et al., *Mol. Cell. Probes* 8:91–98 (1994)). The term nucleic acid is used interchangeably with gene, cDNA, and mRNA encoded by a gene.

By a nucleic acid sequence "homologous to" or "complementary to", it is meant a nucleic acid that hybridizes, duplexes or binds only to DNA sequences encoding one protein or portions thereof. A DNA or RNA sequence which is homologous to a target sequence can include sequences which are shorter or longer than the target sequence so long as they meet the functional test set forth. Hybridization conditions are specified along with the source of the DNA. For example, the hybridization is done in a Southern blot protocol using a 0.2×SSC, 0.1% SDS, 65° C. wash. The term "SSC" refers to a citrate-saline solution of 0.15 M sodium chloride and 20 mM sodium citrate. Solutions are often expressed as multiples or fractions of this concentration. For example, 6×SSC refers to a solution having a sodium chloride and sodium citrate concentration of 6 times this amount or 0.9 M sodium chloride and 120 mM sodium citrate. 0.2×SSC refers to a solution 0.2 times the SSC concentration or 0.03 M sodium chloride and 4 mM sodium citrate.

Accepted means for conducting hybridization assays are known and general overviews of the technology can be had from a review of: *Nucleic Acid Hybridization: A Practical Approach,* Ed. Hames, B. D. and Higgins, S. J., IRL Press, 1985; *Hybridization of Nucleic Acids Immobilized on Solid Supports,* Meinkoth, J. and Wahl, G.; *Analytical Biochemistry,* Bol 238, 267–284, 1984 and Innis et al., *PCR Protocols,* supra, all of which are incorporated by reference herein.

Nucleic acid strands are considered complementary whenever the two strands can come together to make a double helix, pairing an adenine on one strand with a thymidine (or uridine in RNA) on the other strand and a cytosine on one strand with a guanine on the other. In fact, there can be some laxity (depending on the length of the nucleic acid) in the pairing, while still being considered complementary. Up to 10% wrong or mismatched bases can be typically tolerated under the complementary standard.

"Nucleic acid probes" or "probes" may be DNA or RNA fragments. DNA fragments can be prepared, for example, by digesting plasmid DNA, or by use of PCR, or synthesized by either the phosphoramidite method described by Beaucage and Carruthers, *Tetrahedron Lett.* 22:1859–1862 (1981) (Beaucage and Carruthers), or by the triester method according to Matteucci, et al., *J. Am. Chem. Soc.,* 103:3185 (1981) (Matteucci), both incorporated herein by reference. A double-stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid.

The term "oligonucleotides" as used herein refers to DNA or RNA molecules which are usually less than 100 nucleotides long. The shorter length of oligonucleotides means that they can be made by a chemical synthesis machine. Oligonucleotides may be used as nucleic acid probes or primers in PCR.

"Primers" are oligonucleotides comprising either natural or analog nucleotide that can serve as the basis for the amplification of a select nucleic acid sequence. They include both polymerase chain reaction primers and ligase chain reaction oligonucleotides.

"Psoralen" is a tricyclic aromatic compound that contains 2 photoreactive centers and can intercalate into DNA and form a photoreactive crosslink that inactivates the DNA. Psoralen can be tritiated or tagged with a fluorescent entity for labeling purposes.

"Psoralen cross-linking" refers to the process of cross-linking psoralen to DNA. The complex that is formed by cross-linking is not only hydrogen bonded, but also covalently linked. This permits the use of rigorous, even denaturing, wash conditions when detecting cross-linked probe-target mixtures.

The term "random oligonucleotide" as used herein refers to an oligonucleotide consisting of a random mix of nucleotides. The oligonucleotide is typically from about 6 to about 40 nucleotides.

As used herein, a "tissue" is a human tissue -specimen that can represent virtually every normal tissue and every significant human disease. The tissues referred to herein are embedded in wax.

"Waxes" are those substances that are not soluble in water and which are used to preserve sample specimens. Waxes have the following properties: (a) crystalline to microcrystalline; (b) capacity to acquire gloss when rubbed; (c) low viscosity at just above the melting point (as distinct from resins and plastics) and (d) low solubility in solvents for fats at room temperature. They may be of vegetable, mineral, animal or synthetic origin. Paraffin, for example, is a mixture of hydrocarbons occurring natively in ozocerite, peat and bituminous coal, and is a constituent of petroleum from which it is distilled. These materials have useful preservative and fixative properties.

Isolation of complete representation of cellular RNA

The invention describes a method of isolation of complete representational cellular mRNA from a wax-embedded biological sample.

Extraction

First, the RNA is extracted from the wax-embedded biological sample. Wax biological embedded samples are samples that have been preserved in paraffin or other similar wax material. The wax sample may be one that includes a preservative or fixative such as formaldehyde (or FORMALIN). A slice of the sample with the tissue can be removed from the wax block and diced and the RNA extracted by any of a number of RNA extraction methods well known in the art. The preferred method is RNA extraction using an RNA extraction buffer, that is preferably made up of Tris, NaCl, EDTA, and SDS. The sample can be extracted using phenol, phenol/chloroform/isoamyl alcohol, chloroform/isoamyl alcohol, and precipitated, for example, in ammonium acetate, isopropanol and glycogen. Or alternatively, only phenol/chloroform extraction can be used. The RNA can then be centrifuged, washed and resuspended in water, preferably water that has been treated with diethyl pyrocarbonate (DEPC water). Alternatively an RNA extraction buffer containing NaCl, MgCl$_2$, Tris, Nonidet, and DTT (dithiothrietol) could be used. In addition an RNase inhibitor could be added to the RNA extraction buffer (e.g., Macaloid, vanadyl-ribonucleoside complexes).

Removal and denaturation of the DNA from the sample is preferred in order to separate out the RNA of interest. The DNA can be removed from the biological sample after extraction. The preferred method uses a DNase I buffer, where DNase I (Boehringer Mannheim, Indianapolis, Ind.) is added to the sample, which is then centrifuged, extracted, and precipitated. Preferably the extraction is a combination of phenol/chloroform/isoamyl alcohol extraction and chloroform/isoamyl alcohol extraction. "DNase I" is an endonuclease that hydrolyzes double-stranded or single-stranded DNA preferentially at sites adjacent to a pyrimidine nucleotide (thymidine or cytosine). In the presence of magnesium it attacks each strand of DNA independently with randomly distributed cleavage sites to produce a mixture of 5'-phosphate mono- and oligonucleotides. After extraction, the RNA can then be precipitated, centrifuged and washed. The RNA pellet can then be resuspended, preferably in Tris, EDTA, but can also be resuspended in water or other buffered aqueous solution.

If desired, the RNA concentration can then be determined by various quantitation methods such as by measuring the OD$_{260}$ of an aliquot of the final preparation. An RNA sample whose OD$_{260}$=1 contains approximately 40 $\mu$g of RNA per milliliter.

A significant advantage of the isolation of complete representational mRNA here is that no added steps for preferential elimination of rRNA is necessary. The fact that such a step is not necessary has not heretofore been appreciated by those of skill in the art. The common method for separating mRNA from rRNA selects for polyadenylated RNA to select for mRNA only. The term "polyadenylated RNA" refers to a large proportion of mRNAs that carry tracts of poly(A) or multiple adenosines at their 3' termini. The poly A tail allows the mRNA to be separated from rRNA, which does not contain a string of adenosine nucleotides at the end.

Selection for poly A is not effective if a complete representation of the cellular mRNA is required in wax-preserved samples because mRNA is typically degraded into fragments of less than 250 nucleotides which do not all contain a poly A tail. Therefore, selecting only RNA with the poly A tail would select only the mRNA that had not been degraded and would select only short pieces that remain attached to the tail, so not only is representation incomplete, but it is highly biased in terms of what portion of the message is represented, e.g. 5' end v. 3' end. This selection would miss a lot of mRNA and thus decrease the representation of the cellular mRNA population. Therefore to isolate a complete representation of the cellular mRNA, no selection for poly A is used or is necessary to separate out the RNA.

Without intending to be limited to theory, we believe that the lack of contamination of rRNA despite the lack of separation technique may be due to rRNA being crosslinked to proteins removed in the extractions.

Thus, at the end of the isolation process a complete set of cellular mRNA, which is a measure of gene expression, has been isolated.

Synthesis of cDNA library representative of cellular mRNA

To synthesize a cDNA library representative of cellular mRNA, a first strand of cDNA complementary to the sample cellular RNA is synthesized using reverse transcriptase.

This is typically done by contacting the sample RNA to one or more oligonucleotides, preferably random oligonucleotides, from about 6 to about 40, preferably about 6 to about 10 nucleotides long and reverse transcribing to create single strand cDNA copies of the cellular RNA. Reverse transcription occurs as is taught and as is well known in the field. The contacting step is typically carried out at 70° C., for example. This can be done using the commercially available BRL Superscript II kit (BRL, Gaithersburg, Md.) or other commercially available kits. "Reverse transcriptase" is an enzyme that acts as an RNA-dependent DNA polymerase. It prefers to copy RNA, but can also accept DNA templates. It can therefore be used to synthesize double-stranded DNA copies of RNA templates. The reaction is typically stopped by transferring the reaction mixture to ice. Alternatively, the reaction can be stopped by heating to 70° C. or extraction.

Additionally, a second strand of cDNA can be synthesized using DNA polymerase I, by methods well known in the art. The cellular mRNAs can be selectively separated from the cDNA copies at the same time the second cDNA strand is synthesized or afterwards. This is done by, for example, treating the mixture to an RNase such as *E. coli* RNase H that degrades the resident RNA. After synthesis of the second DNA strand, the DNA can be extracted by the use of phenol/chloroform and isoamyl alcohol to remove the proteins, precipitated in ethanol, centrifuged, washed and resuspended in a buffer. The buffer used is preferably TE buffer, but others as is known in the art could be used instead.

Methods of this invention make use of the fact that these samples are already highly degraded. If, however, the sample from the wax-embedded nucleic acid sample does not appear to be heavily degraded, i.e., for example, as observed when placed on a gel, the sample of RNA or the cDNA copies have some fragments which are in the range of over 500 base pairs long, then it is desirable to further degrade the nucleic acid fragments. Fragments could be further cut using a restriction endonuclease that cuts frequently such as HaeIII, Sau3AI or by other means known in the art.

In addition, a pair of complementary oligonucleotide adaptors that will serve as linkers or labels can be ligated to the cDNA copies for purposes of amplification by way of blunt end ligation, by, for example, using T4 DNA ligase. The adaptors are complementary, but it is preferred that the two adaptors be of different lengths and that the adaptors be about 6 to about 40 nucleotides in length. The adaptors are preferably staggered in length so that when they are used for the ligation process they will ligate to cDNA in a single known orientation. Also, in many cases it may be desirable to have one of the adaptor sequences sufficiently short enough so that the shorter sequence is readily removed from the reaction mixture after ligation and before amplification of the cDNA fragments is completed. Typically, the short adaptors are less than 12 nucleotides long and may be removed by column separation techniques or by precipitation.

Though the sequence used for adaptors is not particularly critical, it is preferred that when, for example, human genomes are the subject of the analysis, that adaptor sequences be used that are not homologous to sequences found in the human genome. For example, bacterial or viral type sequences would be likely candidates for the adaptor sequences.

Alternatively, the first adaptor and the second adaptor may each contain a sequence for a restriction endonuclease site that can be used to create sticky or blunt ends that provide known sites that can be targeted as desired, for example, for cloning purposes. It is preferred in this case that the restriction site have a consensus sequence of four bases. A pair of adaptors thus will have at least a four base sequence that is complementary to each other, but the adaptors do not have to be of the same length.

The adaptors are typically joined to blunt-ended double-stranded cDNA at a molar concentration that is at least 100 times greater than the concentration of termini of cDNA in order to minimize blunt-end ligation of the cDNA molecules. Any unreacted adaptors and the low-molecular weight products created by restriction enzyme digestion of polymerized linkers may be efficiently removed by electrophoresis or column chromatography or other commonly available commercial products that remove low molecular weight nucleic acids, such as Qiagen Qiaquick columns (Qiagen, Chatsworth, Calif.).

Thus, the adaptors in the present invention are typically double-stranded nucleotides and will be staggered at one end ("sticky end") and blunt at the other, with one strand being longer than the other. The blunt ends of the pair will be ligated to both ends of the double-stranded cDNA fragments typically for ready amplification. The adaptors will conveniently provide a sequence complementary to a primer to be used if the cDNA is amplified in a subsequent step. Before performing the ligation reaction, a blunt end fill-in reaction can be used to fill the ends of complementary cDNA strands to equal lengths, typically using T4 DNA polymerase. The adaptors can then be added in a ligation reaction. The cDNA copies can then be amplified using a primer complementary to one of the adaptors, preferably complementary to the longer stranded adaptor.

As an alternative, the cDNA may be digested with one or more restriction endonucleases that leave a sticky end overhang. Adaptors that contain the complementary sequence may then be ligated to the digested cDNA. This technique is less preferred for very degraded material, since most fragments are too small to contain multiple restriction sites and the method may produce a more biased representation of the cDNA after ligation and subsequent amplification.

Amplification can be carried out using the polymerase chain reaction (PCR) or, alternatively, using other amplification techniques known to and used by those of skill in the art. PCR is a method of amplifying DNA that uses a single copy of a DNA molecule to create millions of copies. Taq is the thermostable DNA polymerase enzyme used in PCR to create DNA copies. In a presently preferred embodiment, the cDNA is amplified by adding the appropriate primer and using at least about 10 cycles, more usually at least about 20–30 cycles. The number of cycles will vary depending on the initial concentration of cDNA. For a general overview of PCR, see, e.g., *PCR Protocols: A Guide to Methods and Applications* (Innis, M.; Gelfand, D.; Sninsky, J. and White, T. (Eds.); Academic Press, San Diego (1990)), which is incorporated herein by reference.

Amplified cDNA copies can be separated from one another by size or sequence specificity by any of the appropriate methods known and used in the art.
Determine presence or absence of gene expression After synthesis of the cDNA probe library corresponding to the complete representation of the cellular mRNA, the cDNA probes can be labeled in any one of a variety of ways. Nick translation is typically used, but random hexamers, photobiotinylation, or psoralen cross-linking are also all preferred methods and can be used. Alternatively, cDNA may be synthesized directly from the mRNA for use as a probe without subsequent amplification by using labeled oligonucleotides or labeled dNTP's during the cDNA synthesis reaction.

The labeled probes can then be used to screen against nucleic acid material from a known source. One method is hybridization to a high density array arrangement whereby scores of tissues can be tested and compared to determine which genes are expressed or not expressed in various tissue samples of interest. Data obtained from such an analysis can be useful for tracking down which genes are involved in particular diseases or are active in particular cell types. A high density array where multiple probes are used to test multiple nucleic acid samples at the same time enables the analysis of hundreds or thousands of specimens, providing automated readouts and analysis of the resulting expression data. The resulting cDNA probes may be used to obtain sequence information regarding the expressed genes which can also be used to compare with other known sequences in established data banks.

Expression of genes within diseased and/or normal tissue samples can also be examined by immunocytochemical analysis to provide a detailed view of association between a gene and expression of particular proteins.

The screening can be conducted against nucleic acids representing various tissue types. The screening may be performed by contacting known nucleic acid probes with an array of cDNA corresponding to the mRNA from the tissue sample and determining whether hybridization occurs to determine whether a particular gene was expressed in the tissue sample.

Alternatively, labeled cDNA probes derived from the cellular mRNA of two different tissue samples can be contacted with known nucleic acid gene sequences to determine whether the same gene is expressed in both tissue samples. The determination is typically made by detecting hybridization, but can also be done by immunological methods.

In another embodiment using labeled cDNA, the method can be used to quantify expression of a particular gene by contacting cDNA to a known nucleic acid sequence for a gene of interest and detecting hybridization. The amount of mRNA specifying a particular protein can be determined based on the amount of mRNA obtained from the original biological sample. The amount of cDNA derived from an RNA sample is proportional to the RNA present in the original sample and thus indicative of the level of expression. Production of cDNA yields a 1:1 ratio between RNA and cDNA. Our studies show that there is reasonable conservation of starting ratios in amplified material derived from total RNA with blunt end ligation.

The assays of the present invention offer the advantage that many samples can be processed in a short period of time. High throughput assays for the presence, absence, or quantification of particular nucleic acids or protein products are well known to those of skill in the art. Thus, for example, U.S. Pat. No. 5,559,410 discloses high throughput screening methods for proteins, U.S. Pat. No. 5,585,639 discloses high throughput screening methods for nucleic acid binding (i.e., in arrays), while U.S. Pat. Nos. 5,576,220 and 5,541,061 disclose methods of screening for ligand/antibody binding.

In addition, high throughput screening systems are commercially available (see, e.g., Zymark Corp., Hopkinton, Mass.; Air Technical Industries, Mentor, Ohio; Beckman Instruments, Inc., Fullerton, Calif.; Precision Systems, Inc., Natick, Mass., etc.) These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization.

The manufacturers of such systems provide detailed protocols for the various high throughput assays. Thus, for example, Zymark Corp. provides technical bulletins describing screening systems for detecting the modulation of gene transcription, ligand binding, and the like.

EXAMPLES

The following examples illustrate, but are not to be construed as limiting the invention in any way.

Example

Example 1

Isolation of Complete Representation of Cellular mRNA

RNA Extraction from Paraffin-embedded Tissue Specimen

One 50 μm sample slice was removed from the paraffin block and finely diced with two razor blades and placed in a tube. 500 μl of RNA Extraction buffer (10 mM Tris pH 7.4, 100 mM NaCl, 25 mM EDTA, 0.50 SDS) was added, then 5 μl Proteinase K (20 mg/ml) for a final concentration of 200 μg/ml. The sample was quickly centrifuged and incubated for 3 days in a heating block at 52° C., Every 24 hours, 5 μl of Proteinase K was added for one to three days.

To extract the RNA and purify it, the following steps were performed on each sample tube:

1. 750 μl phenol at pH 4.3 was added and the sample was centrifuged for 10 min at 12,000 RPM RT, after which the aqueous layer was removed and kept for the next steps. The sample can be centrifuged again if necessary.
2. 500 μl phenol/chloroform/isoamyl (25:24:1) at pH 6.7 was added to the aqueous layer and then centrifuged for 5 min at 12,000 RPM RT. The aqueous layer was then removed.
3. (repeat of step 2) 500 μl phenol/chloroform/isoamyl (25:24:1) at pH 6.7 was added to the aqueous layer and then centrifuged for 5 min at 12,000 RPM RT. The aqueous layer was then removed.
4. 500 μl chloroform/isoamyl (24:1) was added to the aqueous layer and the sample was centrifuged for 5 min at 12,000 RPM RT, The aqueous layer was then removed.
5. ¼ volume 8M ammonium acetate, an equal volume of isopropanol and 4 μl (5 mg/ml) glycogen was added and then the sample was incubated at −20° C. for 1 hr.
6. The sample was centrifuged at 4° C. at 13,000 RPM for 15 min and decanted.
7. The resulting pellet was washed in 750 μl 70% ethanol, centrifuged at 4° C. at 13,000 RPM for 5 min, and quickly decanted. Any remaining ethanol was removed with a pipette and the sample tube was air dried until the pellet was dry.
8. The pellet was then resuspended in 20 μl DEPC-Water.
9. 2 μl of 10×DNase I buffer (250 mM Tris pH 7, 50 mM MgCl$_2$, 1 mM EDTA), and 1 μl DNase I (10 u/μl) (Boehringer Mannheim, Indianapolis, Ind.) were added to the sample and quickly centrifuged without vortexing. The sample was then incubated in a 37° C. water bath for 1 to 2 hrs.
10. An equal volume of phenol/chloroform/isoamyl (25:24:1) at pH 6.7 was added and centrifuged for 5 min at 12,000 RPM RT. The aqueous layer was removed and the entire step repeated.
11. Next, an equal volume of chloroform/isoamyl (24:1) was added to the aqueous layer and centrifuged for 5 min at 12,000 RPM RT, and the aqueous layer removed.
12. ¼ volume of 8M ammonium acetate, an equal volume of isopropanol and 4 μl (5 mg/ml) of glycogen were added and the sample was incubated at −20° C. for 20 min.
13. The sample was centrifuged at 4° C. at 13,000 RPM for 15 min and decanted.
14. The pellet was washed in 750 μl of 70% ethanol, centrifuged at 4° C. at 13,000 RPM for 5 min, and quickly decanted, with any remaining ethanol removed by pipette. The tube was air dried until pellet was dry.
15. The pellet was resuspended in 15 μl of T1/10E (10 mM Tris pH 8, 0.1 mM EDTA pH 8) and separated into three 5 μl aliquots. To two of the aliquots 15 μl of T1/10E, ¼ volume 8M ammonium acetate, and 2 volumes of 100% ethanol were added, the tubes were well capped, sealed with parafilm and stored at −70° C.

cDNA Production

The $1^{st}$ strand synthesis was accomplished using a BRL Superscript II reverse transcriptase kit. (BRL, Gaithersburg, Md.) The cDNA first strand synthesis consisted of the following steps:

1. The RNA sample (500 ng), 1 μl random hexamers (50 ng/μl), and DEPC Water to a total volume of 12 μl were mixed, heated at 70° C. for 10 minutes and iced for 1 min.
2. The following reaction mixture was prepared for each sample: 2 μl of 10×PCR buffer (200 mM Tris, pH 8.4, 500 mM KCl), 2 μl of 25 mM MgCl$_2$, 1 μl of 10 mM dNTPs, and 2 μl of 0.1 M DTT. The 7 μl reaction mixture was then added to each RNA sample. Each sample was then mixed and incubated at 25° C. for 5 min.
3. 1 μl Superscript II reverse transcriptase was added to each sample, and incubated at 25° C. for 10 min.
4. The samples were transferred to 42° C. for 50 min, 70° C. for 15 min, and then to ice and immediately into second strand reaction.

The $2^{nd}$ strand synthesis was carried out as follows:

1. The following $2^{nd}$ strand master mix was set up for each sample:

| | |
|---|---|
| 5 × $2^{nd}$ strand buffer* | 30 μl |
| H$_2$O | 94 μl |
| 10 mM dNTPs | 3 μl |
| E. coli DNA ligase (10 u/μl) | 1 μl |
| E. coli DNA polymerase I (10 u/μl) | 1 μl |
| E. coli RNase H (2 μl/μl) | 1 μl |
| *500 mM KCl | |
| 50 mM NH$_4$SO$_4$ | |
| 25 mM MgCl$_2$ | |
| 0.75 mM BrNAD | |
| 100 mM Tris 7.5 | |
| 0.25 mg/ml BSA | |

The 130 μl of master mix was added to each 20 μl $1^{st}$ strand reaction, mixed, and incubated at 16° C. for 2 hrs.

2. The samples were extracted with 1 volume of phenol/chloroform/isoamyl alcohol and 1 volume chloroform/isoamyl alcohol.
3. 15 μl of 3M NaOAC, 1 μl of glycogen (20 μg/μl), and 330 μl of 100% ethanol (2×Volume) were added and the samples were incubated at −20° C. for at least 1 to 2 hours. The samples were centrifuged, the pellets were washed with 70% ethanol, and dried.
4. The samples were then resuspended in 10 μl of 1×TE buffer.

Blunt End Ligation of Paraffin cDNA

A blunt end fill-in reaction was performed on the cDNA as follows: 1 μl of 10×T4 polymerase buffer 500 mM NaCl, 100 mM Tris, 100 mM MgCl$_2$, 10 mM dTT), 1 μl 0.5 mg/ml BSA (50 μl/ml final concentration), 1 μl of 1 mM each mixed dNTPs (100 μM each final concentration), 1 μl T4 DNA polymerase (Boehringer Mannheim 1 u/μl), 4 μl cDNA (~1 μg), and 2 μl H$_2$O were mixed for a total volume of 10 μl.

The resulting solution was incubated at 12° C. for 20 min, then 75° C. for 15 min to heat inactivate The ligation reaction was then carried out in a total volume of 30 μl, consisting of the 10 μl from the fill in reaction, 3 μl Boehringer Mannheim 10×ligase buffer (660 mM Tris, 50 mM $MgCl_2$ 10 mM dTT, 10 mM ATP), 4.5 μl mixed oligos (2.2 mg/ml 21-mer, 1.33 mg/ml (12-mer), and 9.5 μl $H_2O$. The oligos are a mixture of any desired staggered complementary oligos that form a blunt end on one end only for blunt end ligation to cDNA. Alternatively, an oligo pair with two dissimilar sticky ends may be used if cDNA was restriction enzyme digested prior to ligation. The oligos are allowed to anneal with a temperature ramp from 50° C. to 10° C. at 1° C./min. Then, 3 μl of T4 ligase (Boehringer Mannheim 5u/μl) was added and the samples were ligated at 16° C. overnight.

Examples of Oligo Adaptor Pairs with a blunt and a staggered end:

```
        AGATCT-3'
3'-TCTAGACTAG              (SEQ ID NO:1)

GGATCC-3'
3'-CCTAGGCTAG              (SEQ ID NO:2)

CTCTTGCTTGAATTCGGACTA-3'   (SEQ ID NO:3)
    3'-CTTAAGCCTGAT         (SEQ ID NO:4)
```

Examples of Less Preferred Oligo Adaptor Pairs with Two Sticky Ends

```
ACATTGGGTTAGCTAGG-3'       (SEQ ID NO:5)
    3'-ATCGATCCCTAG         (SEQ ID NO:6)

GTTACCCACCAAGCCA-3'        (SEQ ID NO:7)
    3'-GTTCGGTTCTAG         (SEQ ID NO:8)
```

PCR Amplification of paraffin cDNA ligation

The ligation reaction products were cleaned up with Qiaquick PCR columns per instructions (Qiagen, Chatsworth, Calif.) samples were eluted in 30 μl T1/10E.

A 10 cycle preamplification was run in a 200 μl reaction volume consisting of the following: 10 μl of the cDNA ligation reaction, 20 μl of 10×PCR buffer, 1.5 μl of mixed dNTPs where each nucleotide is 25 mM, 2 μl 21-mer of choice (1 mg/ml), and 165.5 μl $H_2O$. The samples were incubated at 72° C. for 3 minutes to remove the 21-mer. 1 μl of Taq was then added to the reaction volume. Samples were then incubated at 72° C. for 5 minutes to fill in to the 3' end. The reaction is amplified for 10 cycles as follows: 94° C. for 1 minute, 52° C. for 1 minute, 72° C. for 2 minutes, and 72° C. for 10 minutes. Reactions were then held at 4° C. or frozen until needed.

Additional amplification was then performed for 20 cycles. The 200 μl reaction volume consisted of the following: 5 μl of the 10 cycle preamplification reaction, 20 μl of 10×PCR buffer, 1.5 μl of 25 mM dNTPs, 2 μl 21-mer of choice (1 mg/ml), 1 μl of Taq, and 170.5 μl $H_2O$. Each of the 20 cycles consisted of incubating at 94° C. for 1 minute, 52° C. for 1 minute, 72° C. for 2 minutes, and 72° C. for 10 minutes. The samples were then soaked at 4° C.

Example 2

High Density Array of 1000 Genes Probed with Skin cDNA

An array was made of 1000 different genes that had been cloned into vectors, and then the individual inserts were amplified with universal vector primers. These were then blotted robotically in duplicate using Bio-mek robot onto nylon membranes, and then probed with amplified and nick-translated cDNA (incorporating radiolabeled nucleotides) derived from a paraffin-embedded skin sample. The nylon filter was then scanned with a Molecular Dynamics phosphorimager, the image was enlarged 4 fold, and printed (FIG. 1). The darker spots show detection of high copy number cDNAs that are present in the amplified skin probe, and the lighter spots show proportionate detection of low copy sequences.

Example 3

Paraffin-derived Amplified cDNA Probed with Three Genes

In this example, amplified cDNA from 42 different paraffin archival diseased tissues (+2 cell line controls) were blotted onto nylon, and then probed with nick-translated, radiolabeled pooled cDNAs for three genes (GTPase, KIAA and ORP). As can be seen in FIG. 2, six samples show increased expression of one of these three genes, five samples in rows 9 and 10, and a cell line control in row 15. This example demonstrates that gene expression can be simultaneously measured and quantitated in amplified cDNA derived from paraffin archival tissues.

What is claimed is:

1. A method for the production of cDNA representative of complete representational cellular mRNA from a wax-embedded biological sample comprising:
 (a) extracting RNA from the wax-embedded sample by removing the DNA in the biological sample with a DNAse and without a step to selectively eliminate rRNA by selection for polyadenylated RNA to produce sample cellular RNA; and then
 (b) synthesizing a first strand of cDNA complementary to the sample cellular mRNA by contacting the sample RNA to one or more oligonucleotides and a reverse transcriptase to create single strand cDNA copies of the cellular RNA representative of the complete cellular mRNA; and
 (c) ligating a pair of complementary oligonucleotide adaptors to the cDNA wherein the adaptors are of different lengths.

2. The method of claim 1, comprising further a step of synthesizing complementary DNA strands to the cDNA copies to create double-stranded cDNA after step (b).

3. The method of claim 1, comprising further a step of amplifying the cDNA copies with a primer complementary to one of the adaptors.

4. The method of claim 3, wherein the amplified cDNA copies are separated from one another by size or sequence specificity.

5. The method of claim 4, wherein the cDNA probes are produced directly by cDNA synthesis with labeled oligonucleotides or dNTPs.

6. The method of claim 1, wherein one of the adaptors in the pair is about 6 to 18 nucleotides in length and shorter than the other adaptor.

7. The method of claim 1, wherein the cDNA is synthesized using labeled oligonucleotides or labeled dNTPs.

8. The method of claim 1, wherein the first adaptor and the second adaptor contain a sequence for a restriction endonuclease site.

9. The method of claim 1, wherein the wax-embedded sample is formalin-fixed.

10. The method of claim 1, wherein the biological sample is a human sample and the adaptors are not homologous to a nucleic acid sequence found in a human genome.

11. A method for the production of cDNA representative of complete representational cellular mRNA from a wax-embedded biological sample comprising:
 (a) extracting RNA from the wax-embedded sample by removing the DNA in the biological sample with a DNAse and without a step to selectively eliminate rRNA by selection for polyadenylated RNA to produce sample cellular RNA;
 (b) synthesizing a first strand of cDNA complementary to the sample cellular mRNA by contacting the sample RNA to one or more oligonucleotides and a reverse transcriptase to create single strand cDNA copies of the cellular RNA representative of the complete cellular mRNA;
 (c) synthesizing complementary DNA strands to the cDNA copies to create double-stranded cDNA;
 (d) ligating a pair of complementary oligonucleotide adaptors to the cDNA wherein the adaptors are of different lengths; and wherein one of the adaptors in the pair is about 6 to 18 nucleotides in length and shorter than the other adaptor.

12. A method for the production of cDNA representative of complete representational cellular mRNA from a wax-embedded biological sample comprising:
 (a) extracting RNA from the wax-embedded sample by removing the DNA in the biological sample with a DNAse and without a step to selectively eliminate rRNA by selection for polyadenylated RNA to produce sample cellular RNA;
 (b) synthesizing a first strand of cDNA complementary to the sample cellular mRNA by contacting the sample RNA to one or more oligonucleotides and a reverse transcriptase to create single strand cDNA copies of the cellular RNA representative of the complete cellular mRNA;
 (c) synthesizing complementary DNA strands to the cDNA copies to create double-stranded cDNA; and (d) ligating a pair of complementary oligonucleotide adaptors to the cDNA wherein the adaptors are of different lengths and arc not homologous to DNA in the biological sample.

13. A method for determining the presence or absence of gene expression in a wax-embedded biological sample comprising, extracting mRNA from wax-embedded biological material; synthesizing at least two cDNA probes from the wax-embedded biological material obtained pursuant to the method of claim 2 and screening the probes against 1 nucleic acid material containing a known gene of interest to determine if the cDNA probes hybridize with the gene of interest.

14. A method for comparing the genes in two separate biological sources by contacting a known nucleic acid probe representative of one source with an array of cDNA obtained in accordance with the method of claim 2 under conditions suitable for hybridization and determining whether hybridization of the probe to a cDNA fragment occurs.

15. A method for comparing and quantifying expression of at least three genes of interest in a wax-embedded biological source comprising, (a) extracting mRNA from a wax-embedded biological source to obtain complete representational cellular mRNA present in the source;

(b) synthesizing cDNA probes corresponding to the complete representational RNA; and (c) contacting the cDNA probes with DNA representative of at least three different genes and detecting the proportionate copy number of the cDNA probes complementary to DNA from the different genes.

16. The method of claim 15, further wherein steps (a)–(c) are repeated with multiple sources % mRNA.

* * * * *

UNITED STATES PATENT AND TRADEMARK OFFICE
CERTIFICATE OF CORRECTION

PATENT NO. : 6,183,995 B1
DATED : February 6, 2001
INVENTOR(S) : Burmer et al.

It is certified that error appears in the above-identified patent and that said Letters Patent is hereby corrected as shown below:

Column 19,
Line 3, delete "arc" and insert therefor -- are --.
Line 10, after "against", delete "1".

Signed and Sealed this

Twenty-eighth Day of January, 2003

JAMES E. ROGAN
*Director of the United States Patent and Trademark Office*

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

GATCAGATCT                                                                10

(2) INFORMATION FOR SEQ ID NO:2:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GATCGGATCC                                                                10

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

CTCTTGCTTG AATTCGGACT A                                                   21

(2) INFORMATION FOR SEQ ID NO:4:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TAGTCCGAAT TC                                                             12

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

ACATTGGGTT AGCTAGG                                                        17

(2) INFORMATION FOR SEQ ID NO:6:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

GATCCCTAGC TA                                                             12

(2) INFORMATION FOR SEQ ID NO:7:

```
        (i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:7:

GTTACCCACC AAGCCA                                                          16

(2) INFORMATION FOR SEQ ID NO:8:

(i) SEQUENCE CHARACTERISTICS:
             (A) LENGTH: 12 base pairs
             (B) TYPE: nucleic acid
             (C) STRANDEDNESS: single
             (D) TOPOLOGY: linear (ii) MOLECULE TYPE: DNA (xi) SEQUENCE DESCRIPTION: SEQ ID NO:8:

GATCTTGGCT TG                                                              12
```